(12) United States Patent
Gilby

(10) Patent No.: US 6,636,304 B2
(45) Date of Patent: *Oct. 21, 2003

(54) LASER INDUCED FLUORESCENCE CAPILLARY INTERFACE

(75) Inventor: Anthony C. Gilby, Foxborough, MA (US)

(73) Assignee: Waters Investments Limited, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,445

(22) Filed: Apr. 11, 2001

(65) Prior Publication Data

US 2002/0030810 A1 Mar. 14, 2002

Related U.S. Application Data

(63) Continuation of application No. 09/379,936, filed on Aug. 24, 1999, now Pat. No. 6,239,871.

(51) Int. Cl.[7] .................................................. G01N 1/10
(52) U.S. Cl. ...................... 356/246; 356/410; 356/318
(58) Field of Search .................... 356/244, 246, 356/300, 301, 318, 319, 326, 336, 338, 342, 346, 440, 410, 411; 422/68.1, 82.07, 82.08, 82.05

(56) References Cited

U.S. PATENT DOCUMENTS

| 4,348,107 A | 9/1982 | Leif | 356/72 |
|---|---|---|---|
| 4,714,345 A | 12/1987 | Schrader | 356/246 |
| 4,747,687 A | 5/1988 | Hoppe et al. | 356/246 |
| 5,037,199 A | 8/1991 | Hlousek | 356/246 |
| 5,235,409 A | 8/1993 | Burgi et al. | 356/436 |
| 5,372,783 A | 12/1994 | Lackie | 422/68.1 |
| 5,377,004 A | * 12/1994 | Owen et al. | 356/301 |
| 5,414,508 A | 5/1995 | Takahashi et al. | 356/246 |
| 5,434,664 A | 7/1995 | Sapp | 356/244 |
| 5,926,271 A | 7/1999 | Couderc et al. | 356/318 |
| 5,943,128 A | * 8/1999 | Slater | 356/301 |
| 6,239,871 B1 | * 5/2001 | Gilby | 356/246 |

* cited by examiner

Primary Examiner—Hoa Q. Pham
(74) Attorney, Agent, or Firm—Brown Rudnick Berlack Israels; Brian L. Michaelis; John Serio

(57) ABSTRACT

An optical scheme that substantially eliminates spherical aberration and coma, thereby substantially improving fluorescence excitation and collection efficiency. The optical scheme utilizes a laser beam focused by an optical component through the curved surface of a hyper-hemisphere. The hyper-hemisphere focuses the beam sharply at a known point while avoiding spherical aberration and coma. The optical scheme includes both a hyper-hemisphere and a hemisphere. Both the hyper-hemisphere and hemisphere have a substantially planar surface. The substantially planar surface of the hyper-hemisphere is optimally located so that a capillary or cell can be positioned at an internal aplanatic radius. This results in an aplanatic focus at the capillary or cell such that the spherical aberration and coma are zero. A single hyper-hemisphere having a substantially planar surface can be used, wherein the capillary is located at an aplanatic point on the substantially planar surface of the single hyper-hemisphere.

15 Claims, 5 Drawing Sheets

LASER INDUCED FLUORESCENCE CAPILLARY INTERFACE

CROSS REFERENCES TO RELATED APPLICATIONS

This application is a continuation of the U.S. patent application Ser. No. 09/379,936 filed Aug. 24, 1999 now U.S. Pat. No. 6,239,871 which is incorporated herein by reference in its entirety.

FIELD OF THE INVENTION

The present invention relates to the field of spectroscopy, and more particularly to spectroscopy of samples occupying small volumes.

BACKGROUND OF THE INVENTION

Capillary electrophoresis (CE) is a separation technique based on the differential migration of charged particles in an electric field. A thin capillary (20–100 μm internal diameter) is filled with an electrolyte providing a medium in which analytes can migrate through. The sample is introduced at one end of the CE unit. An electric field typically of 100–600 V $cm^{-1}$ is applied across the capillary facilitating analyte species migration according to their electrophoretic mobility (u) passing a detector as they migrate (usually UV or fluorescence) at or near the end of the capillary.

This separation technique as well as others, such as packed capillary liquid chromatography, capillary electrochromatography and super critical chromatography, require spectroscopic measurements to be made on extremely small volumes of flowing liquid samples. The typical application has a sample flowing through a fused silica capillary tube where inside diameters range from 15 to 150 micrometers and the outside diameters range from 150 to 300 micrometers. Various techniques presently are used for directing light from a suitable source into and/or through such a small volume sample cell, as well as taking the light emanating from the inside of the cell and directing it toward a light detecting or analyzing instrument to effect optical analysis or detection of samples contained in the cell. Alignment of the optical system to efficiently direct the light from the source to the capillary cell, particularly to the bore and sample therein, and/or to direct the radiation emanating from the cell to a detector, presents problems.

The underlying problem is generally related to selecting components and precisely aligning them for the purpose of directing light from a light source such as a laser to, or through, to a volume of interest which has a small cross-sectional area perpendicular to the optical access. Similar problems are associated with collecting the light that emanates from a volume of interest and directing it to a photodetector or analyzer.

An implementation described in U.S. Pat. No. 5,037,199 to Hlousek utilizes an optical scheme which attempts to solve these focusing and alignment problems. In Hlousek's disclosure, a laser beam is focused into the lumen of a separations capillary or cell using a ball lens. The ball lens and the capillary/cell are mounted together as a unit. A lens focuses light from a source onto the ball lens. The size and shape of the light may be controlled and/or selected by placement of one or more suitably shaped apertures on axis with the source and the capillary/cell. The sphere or ball lens concentrates light by acting as a very short focal length lens to convert slowly converging light from the laser beam source to a rapidly converging cone of light that will image the source into or through the volume of interest in the cell.

A ball lens used this way suffers severe aberrations, in particular, spherical aberration and coma, making the laser focus larger than desirable. Refraction of light rays at the cylindrical outside surface of the capillary causes astigmatism and further enlargement of the focal spot. In addition, light is lost due to surface reflections at the ball-lens-to-air and air-to-capillary interfaces. Consequently, efficiency of the fluorescence excitation of the sample suffers. Similarly, the ability to efficiently collect the beam is negatively impacted.

SUMMARY OF THE INVENTION

The present invention provides an optical scheme that substantially eliminates spherical aberration and coma, thereby substantially improving collection efficiency and fluorescence rib excitation.

According to the invention, the optical scheme utilizes a laser beam focused by an optical component, such as a microscope objective, through the curved surface of a hyper-hemisphere. The hyper-hemisphere focuses the beam sharply at a known point while avoiding spherical aberration and coma.

In one embodiment, the optical scheme comprises a hyper-hemisphere and a hemisphere. Both the hyper-hemisphere and the hemisphere have a substantially planar surface. The substantially planar surface of the hyper-hemisphere is optimally located at an internal aplanatic radius where a capillary or cell can be positioned. This results in an aplanatic focus at the location of the capillary lumen whereat the spherical aberration and coma are zero. An aluminized hemispherical exterior surface of the hemisphere retro-reflects the beam, thereby providing a second pass through the sample volume.

In one implementation, each of the substantially planar surfaces of the hyper-hemisphere and the hemisphere has a groove disposed therein. The hyper-hemisphere and the hemisphere are mated by placing in contact their substantially planar surfaces. Upon mating, the grooves in the hyper-hemisphere and the hemisphere form a channel in which a fused silica capillary is placed. The lumen of the fused silica capillary is thereby located at a second aplanatic point of the hyper-hemisphere, as well as at the center of the retro-reflecting hemisphere. Fluorescent light emitted by the small excited volume of interest is collected using the same optics, and directed to a detection means using a dichroic beamsplitter by means well known to those skilled in the art. The airspace between the fused silica capillary and the groove is filled with an index-matched gel or liquid, so that the hyper-hemisphere, capillary and hemisphere become a single optical element, thereby eliminating any reflections or losses at the air/silica interface, and also avoiding astigmatism due to the cylindrical capillary boundary.

Alternatively, no groove is formed in the substantially planar surfaces. Instead, each of the substantially planar surfaces can be ground back such that the fused silica capillary fits between the hyper-hemisphere and the hemisphere maintaining the optical scheme, i.e., facilitating positioning of the capillary adjacent to the planar surface(s) at a point of aplanatic focus. The air-space between the hyper-hemisphere and the hemisphere on either side of the capillary is filled with index-matching substance, i.e., gel or liquid. The gel or liquid is index-matched at least to the capillary.

In another embodiment, according to the invention, only a single hyper-hemisphere having a substantially planar surface is used. The capillary is located at an aplanatic point on the single hyper-hemisphere's substantially planar surface.

Features of the invention include provisions of a spectroscopy system, wherein the precise location of which is relatively insensitive to movement of the hyper-hemisphere/capillary assembly. The system possesses a high tolerance for focusing errors and is implemented as a simple assembly.

The hyper-hemisphere used in the present invention increases the numerical aperture (N.A.) of the system by approximately 50%, thereby increasing the collection efficiency. Further, by effectively forming one optical component with the capillary, it eliminates reflection losses as well as the lensing effect of the outer capillary wall. Additionally, the single hyper-hemisphere approach gives the system a very high tolerance for alignment errors.

BRIEF DESCRIPTION OF THE DRAWING

The foregoing and other features and advantages of the present invention will be more fully understood from the following detailed description of illustrative embodiments, taken in conjunction with the accompanying drawing in which.

DETAILED DESCRIPTION

The present invention comprises an optical apparatus designed to allow for spectroscopic measurements of extremely small samples while maintaining a high tolerance for alignment and focusing errors.

Figure 1:
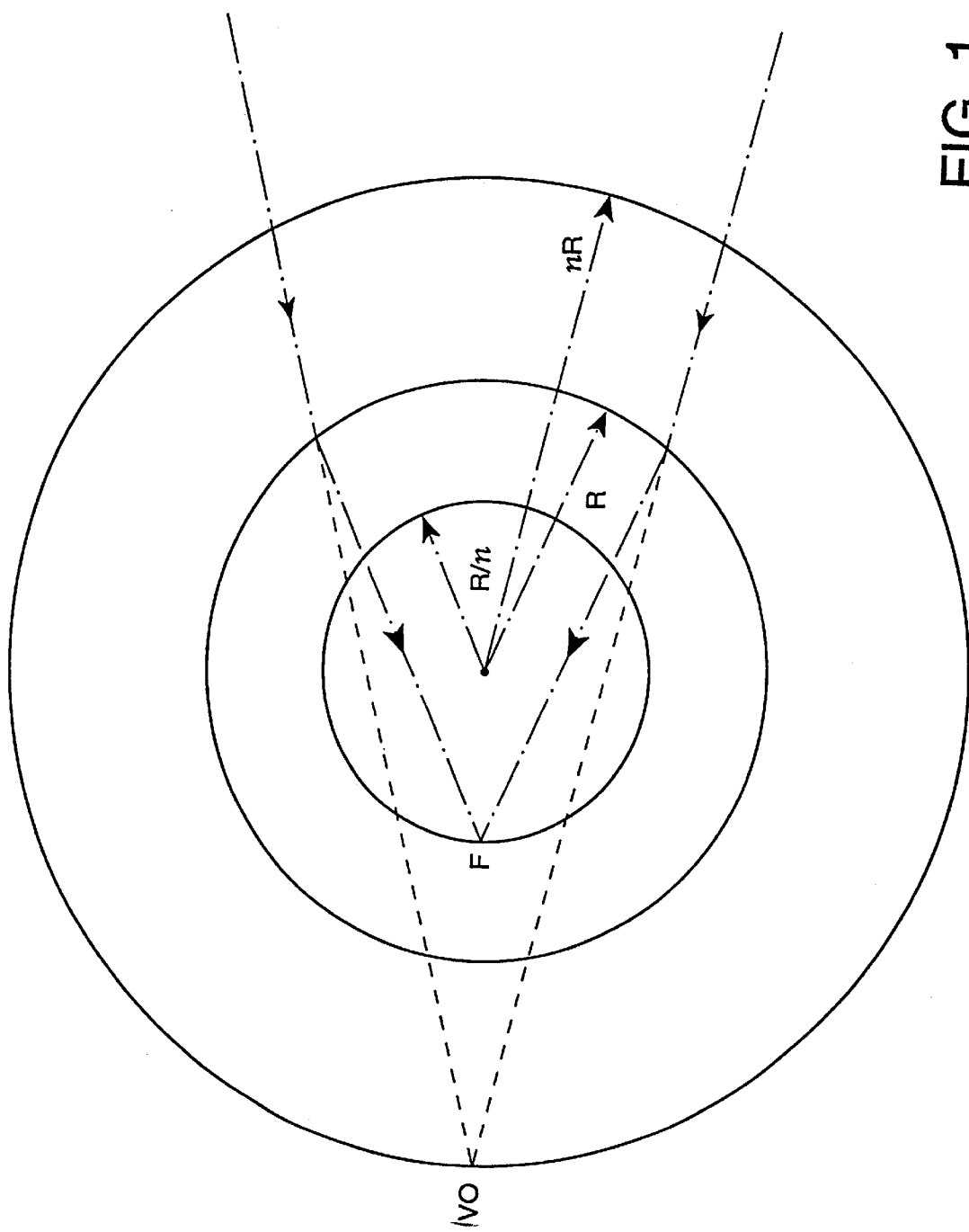
FIG. 1 is a diagram illustrating the optical principles underlying aplanatic capillary interface(s) according to the invention.

Generally, in various embodiments according to the invention, the main optical component is a hyper-hemisphere with a substantially planar surface mated to a hemisphere comprising a substantially planar surface. FIG. 1 illustrates a spherical lens of refractive index "n," and radius of curvature "R." If light is focused so as to form a virtual object at a distance nR from the spherical surface's center of curvature, then the light is brought to a real focus at a distance R/n, a point inside the spherical lens. This focus is aplanatic, i.e., the spherical aberration and coma are zero. The distance from the center of the lens to the aplanatic point is called the internal aplanatic radius. In the present invention, the spherical lens is ground into a hyper-hemisphere with the substantially planar surface located at the internal aplanatic radius. In this way, light can be focused aplanatically on a capillary placed against the substantially planar surface, as in the embodiments shown and described in detail hereinafter.

Figure 2A:
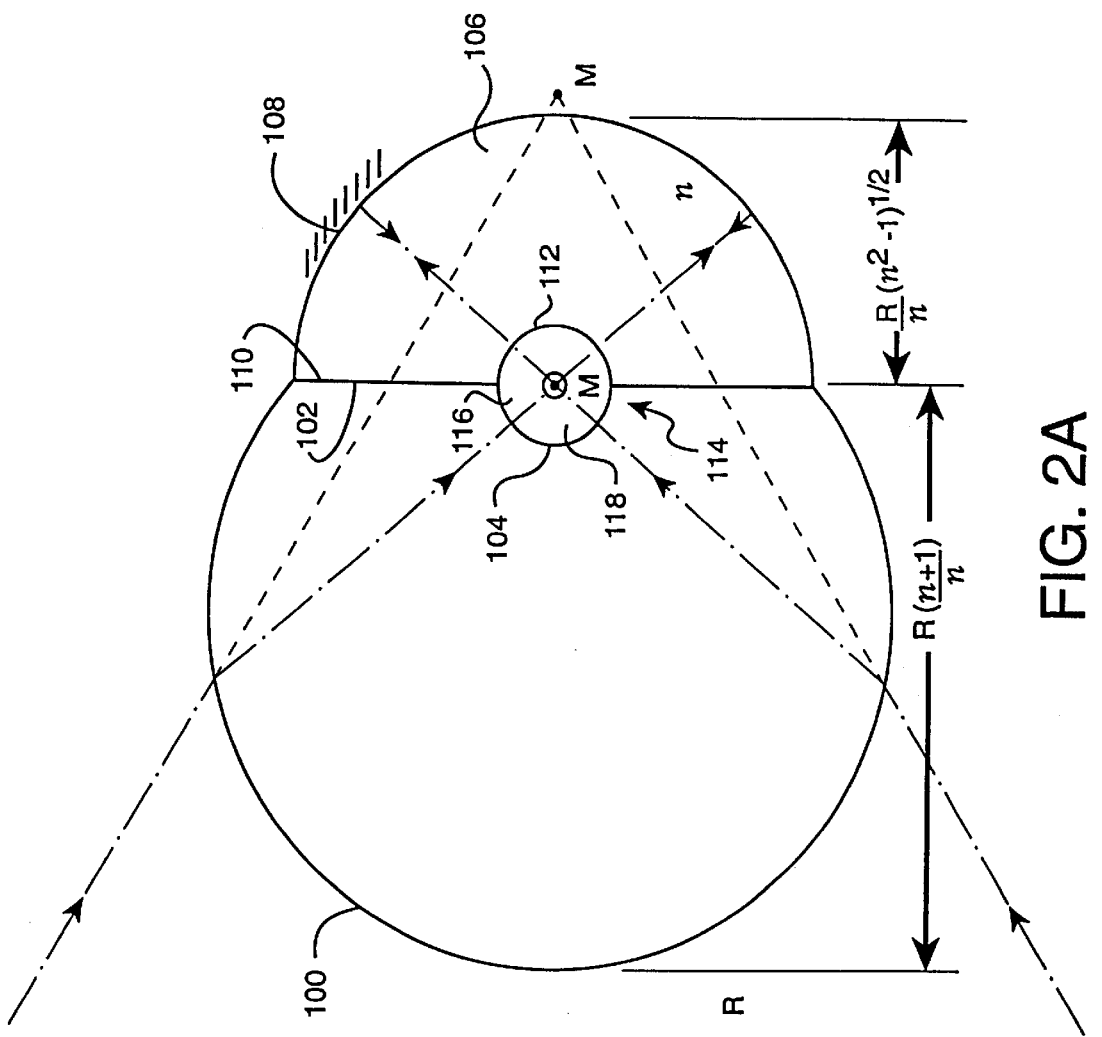
FIG. 2(a) is a diagram of an aplanatic capillary interface according to a first embodiment of the invention.

As illustrated in a first embodiment depicted by FIG. 2(a), a first section of the lens is provided in the form of a hyper-hemisphere 100. The hyper-hemisphere 100 is generally made of fused silica in order to have the same refractive index as the fused silica capillary. The hyper-hemisphere in this illustrative embodiment has a diameter of 3 mm.

A substantially planar surface 102 is formed in the hyper-hemisphere 100. The substantially planar surface is located at the internal aplanatic radius. As illustrated in FIG. 2(a), a curved groove 104 is formed along the diameter of the substantially planar surface of the hyper-hemisphere 100. The groove is a half cylinder sized to fit the outside diameter of the capillary, for example, 360 µm.

A second section of the lens is configured to form a hemisphere 106. The hemisphere 106 is made of fused silica to match the index of refraction of the capillary. Other transparent and non-fluorescing materials could be used for the hyper-hemisphere and hemisphere. However, optimal results require that the index be close to that of the flowcell (or simply, "cell") or capillary. The hemisphere's dimensions in this illustrative embodiment have been chosen so that the size of its planar surface matches that of the hyper-hemisphere. The hemisphere could be larger or smaller than that illustrated without affecting performance. The hemispherical exterior surface 108 in the present embodiment is aluminized to form a retro-reflecting hemisphere that collects forward-scattered or fluorescent light as shown in FIG. 2(a). The hemisphere substantially increases the solid angle over which scattered light is collected. Additionally, the hemisphere increases the effective path length of the excitation beam through the sample leading to a very substantial increase in signal intensity.

A substantially planar surface 110 is formed on the hemisphere 106. Just as with that of the hyper-hemisphere, the substantially planar surface 110 of the hemisphere 106 has a curved groove 112 formed along its diameter similar in dimensions to the groove in the hyper-hemisphere.

The substantially planar surfaces of the hyper-hemisphere and the hemisphere, 102 and 110 respectively, are mated such that the groove forms a channel 114 as illustrated in FIG. 2(a). A fused silica capillary 116 with an inside diameter of, for example, 50 µm, and an outside diameter of, for example, 360 µm, is disposed in the channel. Narrow bore capillaries are typically used in this capillary electrophoresis embodiment because of heat transfer properties and considerations. As the bore size decreases, the surface area to volume ratio increases and, as a result, the heat transfer rate increases. This allows higher electric field strengths to be applied before Joule heating begins to degrade performance. These higher electric field strengths result in faster and more efficient separations. In addition, the lower electrical conductivity of the smaller solution volumes in narrow capillaries results in smaller currents and less Joule heating for a given applied field.

The air space 118 between the fused silica capillary and the groove is filled with an index-matched liquid or gel such as a mineral oil, salt solution, sugar solution, or the like. Index-matching liquids and gels can be obtained commercially. It is important to choose one which is transparent and non-fluorescing at the wavelengths employed. The index-matched liquid or gel couples the lens with the capillary so that the two parts effectively form one optical component. Further, since the lens and capillary are made of the same material, the general lensing effect of the capillary wall is eliminated.

Figure 2B:
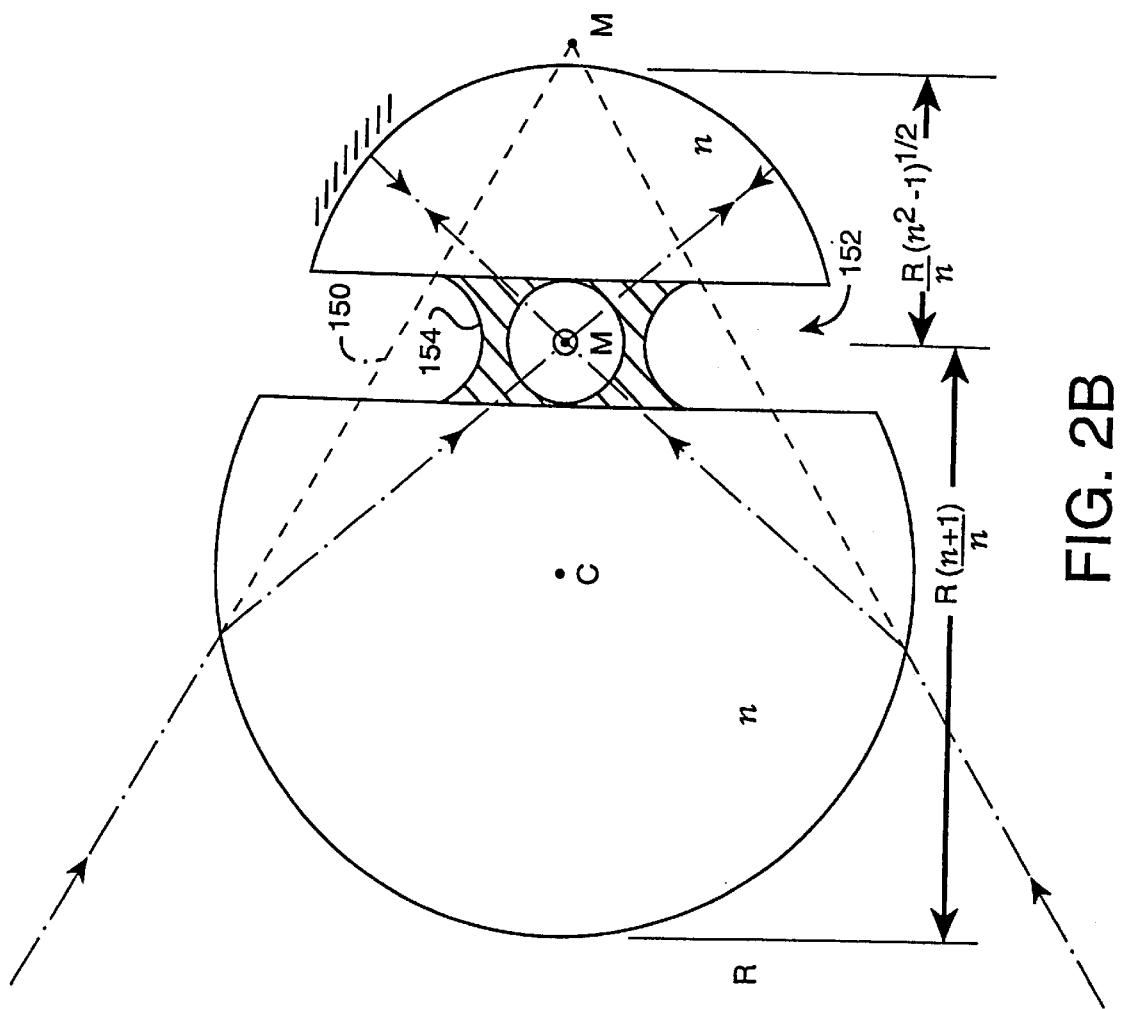
FIG. 2(b) illustrates a variation of the first embodiment of the invention in which no grooves are formed in planar surfaces.

A variation of the first embodiment can be constructed, as illustrated in FIG. 2(b), wherein constructing the curved grooves 104 and 112 is eliminated. Instead of forming curved grooves, the substantially planar surfaces of both the hyper-hemisphere and hemisphere are ground back such that the fused silica capillary fits between them while maintaining the optical alignment. The center of the capillary, or any optical point of interest, is located at an aplanatic point. The air spaces 150 and 152 on either side of the capillary are filled with index-matched gel or liquid (shown generally by label 154) so that, in essence, a single optical component is formed. This variation has all of the operating characteristics and features contained within the above-described embodiment and differs only in construction.

Figure 3:
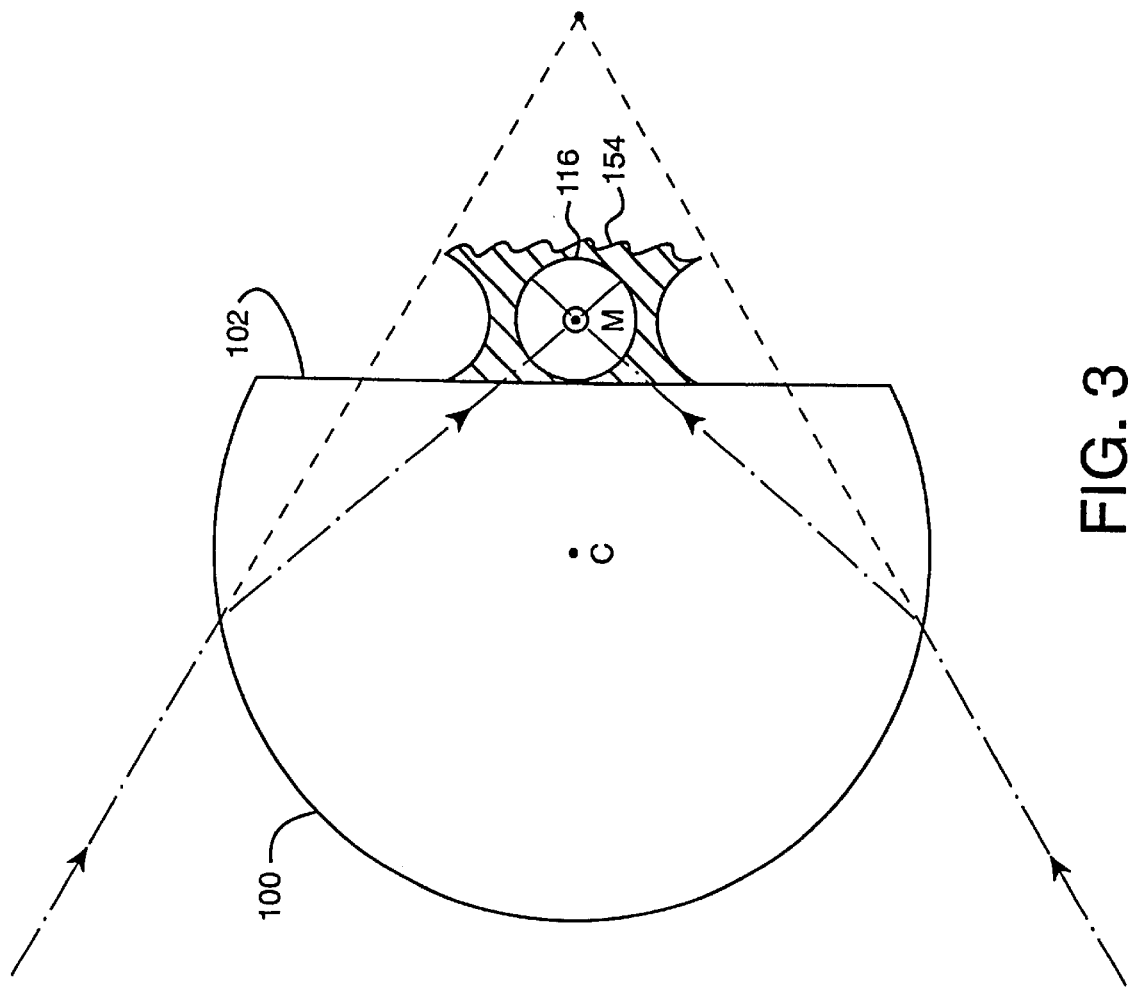
FIG. 3 is a diagram of an aplanatic capillary interface according to another embodiment of the invention.

A second embodiment, illustrated in FIG. 3, of the present invention utilizes only a single hyper-hemisphere with a substantially planar surface. As with the first embodiment, the hyper-hemisphere is made of fused silica in order to match the index of the capillary. The substantially planar surface of the hyper-hemisphere is located in such a manner so that the lumen of the capillary is at the internal aplanatic radius. The hyper-hemisphere may have a groove or not, analogous to that depicted in FIGS. 2a and 2b, respectively. As illustrated in FIG. 3, a fused silica capillary 116 is laid against the substantially planar surface 102 of the hyper-hemisphere 100. Index-matching gel or liquid 154 is placed around the capillary 116 so that the parts essentially form one optical component. The operating principle in this embodiment is similar to that governing the first embodiment except that this embodiment does not use the enhancement factors including double-passing the sample with excitation light and the absence of collecting the forward as well as back-scattered light.

Figure 4:
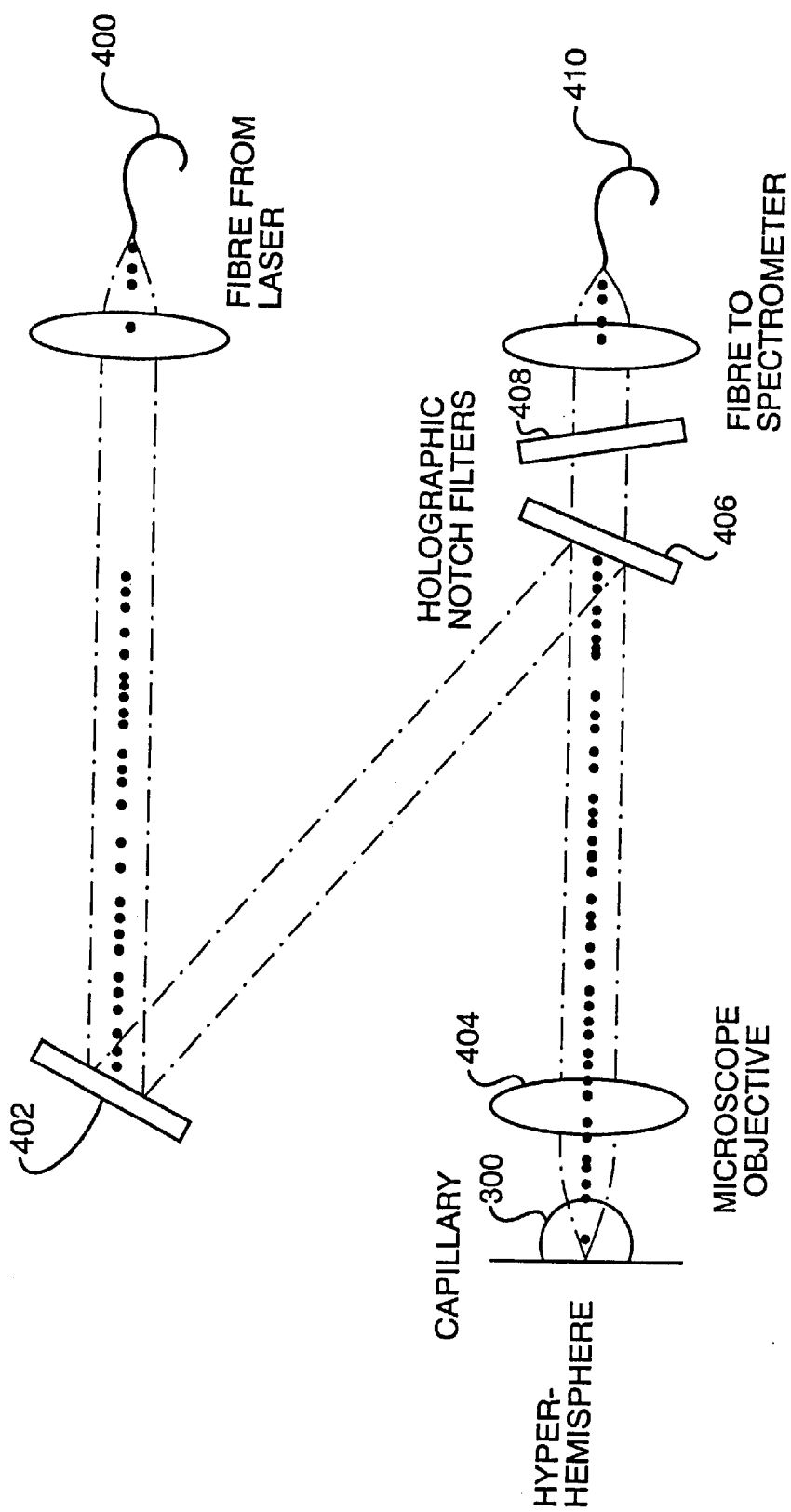
FIG. 4 illustrates an optical system including an aplanatic capillary interface according to the invention.

FIG. 4 shows an optical system including the aplanatic capillary interface of the embodiment depicted in FIG. 3 used in a CE-Raman detector, based around a Renishaw fibre probe. In this illustrative system, 514.5 nm light from an argon ion laser (not shown) is supplied to the interface optics via a 50 μm optical fibre 400. The beam is reflected by a holographic notch filter 402 and focused by a microscope objective 404 into the hyper-hemisphere-capillary assembly 300. The hyper-hemisphere provides an aberration-free focus of the laser beam with the lumen of the capillary, as described above. For this illustrative system, a microscope objective 404 with a working distance greater than 3.7 mm is preferred. Back-scattered light from the sample is collected via the microscope objective 404 and passed through notch filters 406, 408 where the dominant Rayleigh scattered light is filtered out. The Raman scattered light is focused into an optical fibre 410 for transmission to a spectrometer, for example, a Renishaw Mk 3 spectrometer, which utilizes a cooled CCD array for detection. It will be appreciated that this invention is equally applicable for both laser Raman as well as laser induced fluorescence.

Although the first embodiment described utilizes a retro-reflecting hemispherical surface to collect forward-scattered light, it should be appreciated that a mirror coating on the back of the capillary could be used to enhance the performance of the second embodiment. In this case, some portion of the laser light will double pass the sample volume of interest, thus a portion of the forward scattered or fluorescent light will be returned to the detection system.

Although the invention has been shown and described with respect to exemplary embodiments thereof, various other changes, omissions and additions in the form and detail thereof may be made therein without departing from the spirit and scope of the invention.

What is claimed is:

1. An optical apparatus for use in spectroscopy for analyzing samples, comprising:
   a single hyper-hemisphere, formed from a sphere having a substantially planar surface formed by truncating the circumference of said sphere whereby said single hyper-hemisphere has no protruding planar surface; and
   a cell, disposed upon said substantially planar surface of said hyper-hemisphere;
      wherein light passing through said hyper-hemisphere is focused aplanatically on said cell.

2. The optical apparatus of claim 1, wherein said hyper-hemisphere and said cell are produced from material having substantially the same index.

3. The optical apparatus of claim 1, wherein said cell is surrounded by a liquid.

4. The optical apparatus of claim 3, wherein said liquid is indexed matched to said cell.

5. The optical apparatus of claim 1 wherein said substantially planar surface of said hyper-hemisphere includes a curved groove, and said cell is disposed at least partially within said curved groove.

6. The optical apparatus of claim 1 further including a reflecting coating on a portion of a surface of said cell.

7. The optical apparatus of claim 1, wherein said cell is surrounded by a gel.

8. The optical apparatus of claim 7, wherein said gel is indexed matched to said cell.

9. The optical apparatus of claim 1, wherein said hyper-hemisphere and said cell are produced from fused silica.

10. The optical apparatus of claim 1, wherein said cell includes a lumen and said cell is positioned so that said lumen of said cell is located at an internal aplanatic radius.

11. A system for analyzing a sample using light spectroscopy, comprising:
   a light source;
   a microscopic objective, disposed to receive light from said light source;
   optical apparatus, disposed to receive light from said microscopic objective, said optical apparatus comprising:
      a single hyper-hemisphere, formed from a sphere having a substantially planar surface formed by truncating the circumference of said sphere whereby said single hyper-hemisphere has no protruding planar surface;
      a cell having a lumen, disposed proximate said substantially planar surface of said hyper-hemisphere, said cell disposed so that the lumen of the cell is at an internal aplanatic radius of said hyper hemisphere;
      whereby light passing through said hyper-hemisphere is focused aplanatically on said sample contained in said cell; and
   a light detection component, disposed to receive light that has passed through said sample.

12. The apparatus of claim 11, wherein said light source is an argon ion laser.

13. The apparatus of claim 11, further including an optical fiber whereby said light source is passed through said hyper-hemisphere via said optical fiber.

14. The apparatus of claim 13, further including a holographic notch filter wherein said light source is passed through said hyper-hemisphere via said optical fiber by being reflected by said holographic notch filter.

15. The apparatus of claim 14, further including a microscope objective wherein said light source is passed through said hyper-hemisphere via said optical fiber by being reflected by said holographic notch filter and focused by said microscope objective into said hyper-hemisphere.

* * * * *